United States Patent [19]

Daly

[11] Patent Number: 4,565,197

[45] Date of Patent: Jan. 21, 1986

[54] LASER OPHTHALMIC SURGICAL SYSTEM

[75] Inventor: Richard T. Daly, Huntington, N.Y.

[73] Assignee: Lasers For Medicine, Del.

[21] Appl. No.: 554,478

[22] Filed: Nov. 22, 1983

[51] Int. Cl.[4] .......................... A61F 5/06; G02B 27/00; A61B 17/36; A61N 5/06

[52] U.S. Cl. .................................. 128/303.1; 128/395; 128/397; 128/398; 350/96.18; 350/96.26; 350/96.27; 219/121 L; 219/121 LS; 219/121 LU; 219/121 LM; 372/24; 372/101

[58] Field of Search ............... 372/24, 101; 128/303.1, 128/395, 396, 397, 398; 350/96.18, 96.19, 96.14, 96.27, 96.26; 219/121 L, 121 LT, 121 LU, 121 LM, 121 LS

[56] References Cited

U.S. PATENT DOCUMENTS

| | | | |
|---|---|---|---|
| 3,653,384 | 4/1972 | Swope ................................ | 372/15 |
| 3,724,924 | 4/1973 | Lenfaut et al. ................... | 219/121 L |
| 4,163,148 | 7/1979 | Fritsche et al. ................... | 350/96.26 |
| 4,289,378 | 9/1981 | Remy et al. ...................... | 219/121 LS |
| 4,458,683 | 7/1984 | Saito et al. ....................... | 128/395 |

Primary Examiner—D. E. Gantz
Assistant Examiner—Lance Johnson
Attorney, Agent, or Firm—Kane, Dalsimer, Kane, Sullivan and Kurucz

[57] ABSTRACT

An aiming beam coincident with a laser beam is provided in a modified slit-lamp apparatus. The aiming beam is resolved into a number of images displaced with respect to the axis of the slit lamp imaging rays bracketing the intersection of the laser beam and the axis of slit lamp rays, which intersection is their common focus. As the common focus is moved close to a target tissue within the eye, the target tissue to be treated renders each of the images successively sharply visible while the other images remain blurry or not visible. Thus an efficient rough or long-range system is provided for focusing the laser on the target tissue.

10 Claims, 3 Drawing Figures

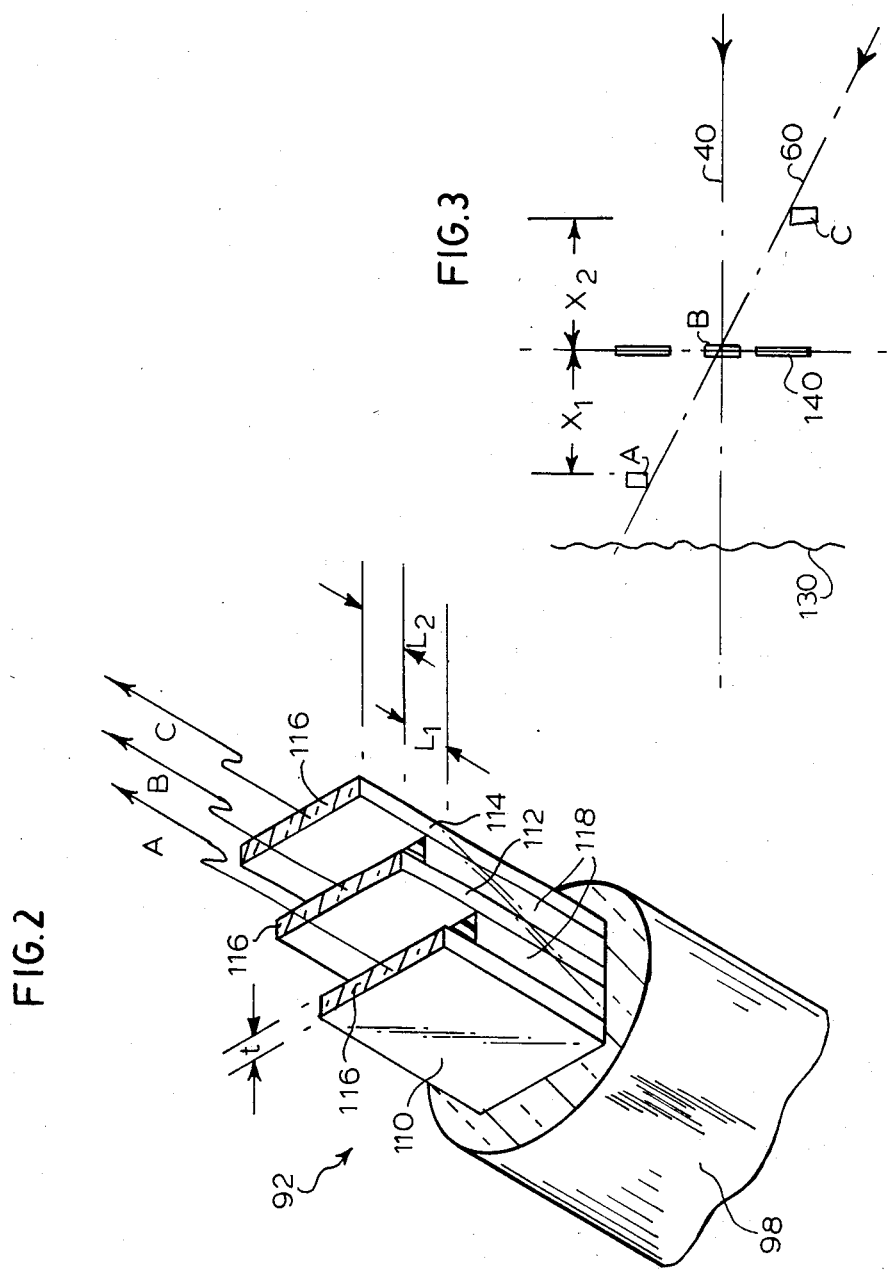

LASER OPHTHALMIC SURGICAL SYSTEM

FIELD OF INVENTION

The present invention pertains to eye surgery by use of lasers and more particularly to a method and apparatus for focusing and aiming a laser beam accurately within a patient's eye.

DESCRIPTION OF THE PRIOR ART

Performing eye surgery by focusing a non-visible, high-power pulsed laser beam on nominally transparent tissues of a patient's eye has been shown to be efficacious. Such operations have been successfully performed to overcome various defects in the eye, for example following catarectomy, where the natural lens has been replaced with an intraocular lens. Frequently within 2 to 4 years thereafter, the posterior tissue of the lens capsule becomes opaque and must be opened. Non-invasive laser surgery of this type has been used successfully for this operation.

Typically a laser ophthalmic microsurgical system is made by modifying an ophthalmic slit lamp apparatus to permit the precise aiming and focusing of the laser beam onto nearly transparent tissues within the eye ("Target Tissues"). An ophthalmic slit lamp apparatus is a device long used to make careful diagnostic observations inside the eye. One such instrument is made by Tokyo Optical Company Ltd., Tokyo, Japan under the trademark TOPCON and is described in their publication No. 8202-30SK. The ophthalmic slit lamp apparatus comprises a binocular viewing microscope and a light source assembly (the "Slit Lamp"). The slit lamp projects a generally elongated or slit-shaped illuminated image into the eye which is then observed through the binocular viewing microscope. The binocular microscope is mounted on a first arm while the slit lamp is mounted on a second arm. The two arms are independently rotatable around a common vertical axis which contains their common focus. The illuminated slit image is focused on a particular "transparent" tissue (the Target Tissue) such as the cornea, front lens surface, rear lens surface or transparent bands lying generally in planes normal to the slit image rays. As the rays from the slit lamp pass through the tissue, even a small amount of light scatter by the tissue renders the slit image visible when observed through the binocular microscope. By rotating the slit lamp and/or the binocular arms differentially, the physician is able to view the chosen tissue in various aspects by the scattered light. The slit-image together with the microscope field of view is moved within the eye by a manual joystick control on the apparatus either laterally (for lateral aiming) or toward or away from the eye (for focusing). A second control knob is used for vertical adjustment.

In the current art, the above-described device has been modified for performing microsurgery by directing and focusing a high power, pulsed laser beam into the eye by means of an additional set of optics "piggybacked" on the slit lamp apparatus. To locate or identify the exact path and focal position of the invisible laser beam, a low intensity visible aiming beam coincident with the laser beam is arranged to focus at a point in space coincident with the slit-image and the laser beam focal spot. In the current art this is accomplished by mounting, on the ophthalmic slit lamp apparatus, a dichroic mirror which reflects the aiming beam and the coincident laser beam into the eye along an optical axis lying in the same plane as that of the binocular microscope and the slit image rays. Typically a low intensity helium-neon laser is used for the aiming beam.

This scheme leads to two major difficulties. First, the physician is often forced to observe the eye tissue during operation through the added dichroic mirror. Such mirrors inherently cause astigmatism, degrading the physician's view. Secondly, the initial focus position of the aiming beam and slit image, in general, does not lie exactly in the plane of the Target Tissue. Thus the physician first sees an unfocused aiming beam scattered from the Target Tissue and must "hunt" for the focus by shifting the slit-image with his joystick until scattering of the aiming beam appears sharpest and of minimum size. Because the aiming image size changes only slowly near the correct focus position, this technique makes it difficult to adjust quickly to the correct focal position since it presents the same "out-of-focus" aspect independent of whether the target tissue is in front of or behind the initial aiming image focal position.

A solution to the problem has been presented in the commonly assigned U.S. application Ser. No. 511,191 filed July 6, 1983, in which the inventor of the present application is also a co-inventor. In that application the aiming image rays are propagated along an axis which does not coincide with but forms a generally vertical angle with the axis of slit lamp rays. Therefore the actual position of the slit image and aiming image with respect to the target tissue may be determined from the apparent relative vertical positions of the aiming image and a fiducial feature of the elongated slit image. This device has been found to be very helpful for fine focusing, i.e. when the plane of the target tissue is relatively close to the common focus. However when the actual distance between the focal plane and the target tissue is greater than the depth of field of the aiming image, the perceived aiming image becomes too fuzzy and out-of-focus and its relative position cannot be used for the above-outlined procedure.

OBJECTIVES AND SUMMARY OF THE INVENTION

In view of the above, an objective of the present invention is to provide a system in which the coarse focusing information is generated regarding the relative positions of the aiming image and target tissue. Further objectives and advantages shall become apparent in the description below.

According to this invention a laser ophthalmic microsurgical system comprises a slit lamp which focuses the image of an illuminated vertical slit along a first axis, a binocular microscope which provides for viewing along a second axis and a laser/aiming system which projects a laser beam and aiming beam coincidently along a third axis. The said first and second axes lie in a common horizontal plane which does not include said third axis. All three axes converge to a common point (the "Common Focus") with the said third axis preferably approaching the Common Focus from below the horizontal plane defined by said first and second axes.

A further modification of the apparatus according to the present invention is the provision of means for projecting a plurality of aiming images along said third axis, bracketing in depth the common focus point. Each of the aiming images is uniquely identifiable. As the physician brings the common focus closer in depth to the target tissue, different aiming images come into focus sequentially to indicate the displacement between the common focus point and the target tissue. When the image selected to indicate the region of the common focus becomes recognizable, i.e. comes into focus, the region of the common focus point has been reached. The fine focusing technique described in the above-mentioned patent may now be used.

BRIEF DESCRIPTION OF THE FIGURES

FIG. 2 illustrates a means of generating the aiming images; and

FIG. 3 is a schematic side view of the eye showing the relative positions of the images therein.

DETAILED DESCRIPTION OF THE PREFERRED EMBODIMENT

Figure 1:
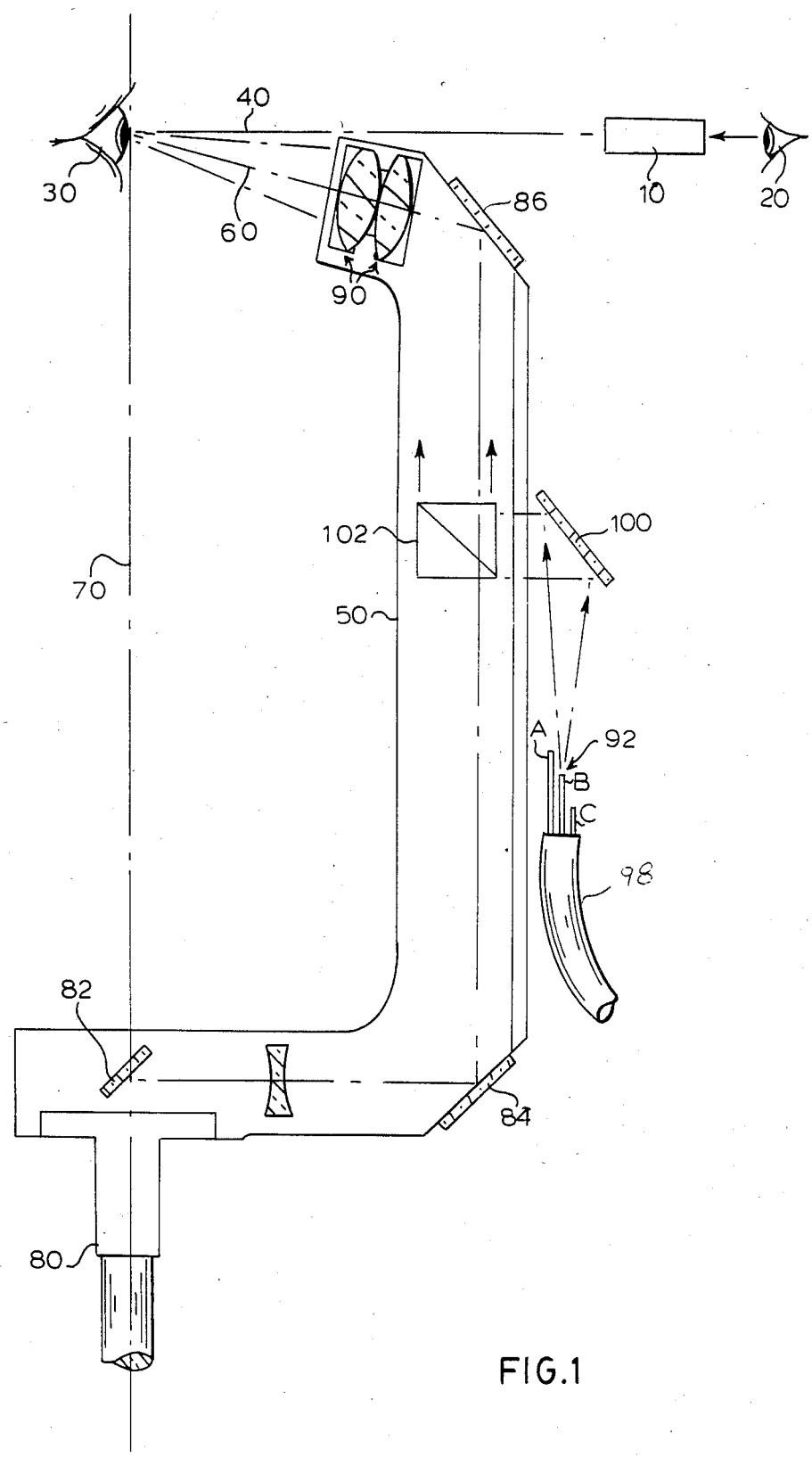
FIG. 1 shows a portion of a slit-lamp apparatus modified in accordance with the present invention for laser eye surgery.

As shown in FIG. 1, the modified apparatus comprises an ophthalmic slit lamp apparatus or system 10 comprising a binocular viewing microscope and a slit light source assembly through which an observer 20 can monitor eye 30 of a patient along first optical axis 40. The apparatus also includes a laser beam guide 50 provided to direct a laser beam and imaging beams into eye 30 along a second axis 60, said second axis being positioned at an acute angle in a non-horizontal plane containing first axis 40. In order to rotate the laser and imaging beams laterally within the eye, the laser (not shown) is disposed so that it projects the beam vertically upwards along axis 70 into the beam guide which is rotatably mounted to a support (not shown) so that it may rotate around axis 70. The laser beam enters through end 80 of guide 50 and is reflected and transmitted through the guide by mirrors 82, 84 and 86. Lens 90 is used for focusing the laser beam within the eye 30 of the patient as previously mentioned. Optic system 10 is independently laterally rotatable around axis 70.

An aiming beam is also sent into the eye coincident with the laser beam. One way of superimposing the aiming beam on the laser beam is shown in FIG. 1. A light source array 92 is positioned and arranged to send the light received from fiber optic cable 98 to a mirror 100. The mirror reflects the beams from the array to a dichroic device 102 disposed within guide 50. The function of device 102 is to transmit or reflect coincidently the beams received from mirrors 84 and 100 towards mirror 86, thereby superimposing the beams from array 92 onto the laser beam. Device 102 may comprise for example a dichroic cube.

The light source array 92 used to generate the aiming beams is shown in more detail in FIG. 2. It comprises a plurality of relatively thin elongated plates 110, 112 and 114 of a light transmitting medium such as glass. Light from a fiberoptical cable 98 is propagated through each plate in the direction shown. Each plate terminates with a light-emitting front face 116. Each front face is displaced longitudinally, i.e. in the direction of the light waves emitted by the surfaces, with respect to the preceeding plate as shown. The plates are kept at a predetermined lateral distance by spacers 118.

The aiming beam comprises the images of the plate ends 116. These images are projected into the eye along axis 60 as described above. FIG. 3 shows in a diagramatic form, a sideview of the different beams entering the eye. The physician views the eye along axis 40. The image of each front surface 116 of plates 110, 112 and 114 are resolved as horizontal light bands disposed perpendicularly to the plane of FIG. 3. In FIG. 3 these light bands are identified as images A, B and C respectively.

In FIG. 3, the target tissue 130 initially lies behind the images A, B, and C. As the common focus is brought closer and closer to the tissue, the tissue moves relatively to the images A, B and C. When the tissue becomes co-planar with image A, the physician viewing the eye along axis 40 can see image A clearly. Images B and C are out of focus and therefore are either too blurry or not visible. As the relative movement of the tissue continues, image A goes out of focus and image B appears. When image B becomes relatively sharp the tissue is co-planar with B and the final focusing adjustment can be made by using the split slit image 140 as described in the copending application Ser. No. 511,191. If image B blurs and image C becomes sharp the physician knows that he has "overshot" the desired position.

Thus the three aerial images A, B, C within the eye provide a valuable means of long-range, rough positioning of the laser and aiming beams. Although images A, B and C could be made identical, they would be even more useful if they were different from each other so that they are uniquely identifiable. For example the images could have different colors. This may be accomplished by providing plates 110, 112 and 114 of different colors. For example plates 110 and 114 could be red while plate 112 could be yellow resulting in red, yellow and red images respectively.

Alternatively the images could have different shapes by shaping the faces 116 appropriately. The two techniques could be combined to produce images of various colors and shapes.

The spacing between the images as seen along the viewing axis 40, should be in the range of the depth of field of each image, such as for example 200 microns. This spacing is determined by the longitudinal distance between the corresponding plates in light source array 92. Thus if the longitudinal spacing between images A and B is $X_1$ and the spacing between images B and C is $X_2$ as shown in FIG. 3, then the distances between the imaging faces 116 of the plates are determined by the formulas:

$L_1 = X_1/M^2$ and
$L_2 = X_2/M^2$

Where $L_1$ is the longitudinal distance between front faces of plates 110 and 112, $L_2$ is the distance between the front faces of plates 112 and 114 (as shown in FIG. 2), and M is the object to image magnification of the system. Obviously one skilled in the art could perform numerous modifications on the above-described device without departing from the scope of the invention as defined in the appended claims. For example the number of plates and images could be changed. Furthermore all plates could be colorless and the beams could be colored by using an appropriate coating in the faces 116, or an appropriate filter.

I claim:

1. A method of providing an aiming beam into an eye for focusing a laser on a tissue of the eye comprising focusing onto eye tissue a plurality of images which are longitudinally spaced and parallel to an axis of projection whereby as the focal plane of the aiming beam moves along said axis each image becomes sharply visible when said image becomes substantially coplanar with said tissue.

2. An apparatus for performing microsurgery in an eye comprising:
- means for viewing the interior of the eye along a first axis;
- means for focusing a laser beam along a second axis into the eye to perform microsurgery; and
- means for projecting a slit image with a fiducial feature into the eye along a third axis; and,
- means for focusing an aiming beam into said eye, said aiming beam comprising several images projected in parallel along said second axis each image having a longitudinally displaced focal plane relative to the fiducial feature of the slit image.

3. The apparatus of claim 2 wherein said aiming beam is superimposed on said laser beam.

4. The apparatus of claim 2 further comprising a light source array for generating said images.

5. The apparatus of claim 4 wherein said array comprises a plurality of parallel plates positioned and longitudinally disposed to form said images.

6. The apparatus of claim 4 wherein at least one of the images has a different color than the remaining images.

7. The apparatus of claim 4 wherein at least one of the images has a different shape.

8. An apparatus for performing microsurgery in an eye comprising:
- means for projecting a slit image with a fiducial feature into the eye along a first axis;
- means for projecting a laser beam and an aiming beam into said eye along a second axis, said second axis intersecting with said first axis at a common focusing point; and
- means for focusing said laser beam and said aiming beam within said eye, said aiming beam being focused by focusing means which comprises a plurality of images longitudinally spaced relative to said first axis and bracketing said common focus point.

9. The apparatus of claim 8 wherein said means for projecting said laser beam and aiming beam comprises a single wave guide having means of superimposing said aiming beam from a laser beam from a laser source.

10. The apparatus of claim 9 wherein said superimposing means comprises a dicroic cube which is disposed within the guide so as to pass the laser beam in one direction and reflect the aiming beam received from said array coincidently in the same direction.

* * * * *